(12) United States Patent
Stenger et al.

(10) Patent No.: US 11,795,131 B2
(45) Date of Patent: Oct. 24, 2023

(54) NARROW RANGE ALCOHOL ALKOXYLATES AND DERIVATIVES THEREOF

(71) Applicant: The Procter & Gamble Company, Cincinnati, OH (US)

(72) Inventors: Patrick Christopher Stenger, Fairfield, OH (US); Gregory Thomas Applegate, Cincinnati, OH (US); Brian Joseph Loughnane, Sharonville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/489,831

(22) Filed: Sep. 30, 2021

(65) Prior Publication Data

US 2022/0106246 A1    Apr. 7, 2022

(30) Foreign Application Priority Data

Oct. 1, 2020    (EP) ..................................... 20199508

(51) Int. Cl.
| | | |
|---|---|---|
| *C11D 1/72* | (2006.01) | |
| *C11D 1/722* | (2006.01) | |
| *C07C 43/13* | (2006.01) | |

(52) U.S. Cl.
CPC ............ *C07C 43/135* (2013.01); *C11D 1/722* (2013.01)

(58) Field of Classification Search
CPC .................................. C11D 1/72; C11D 1/722
See application file for complete search history.

(56) References Cited

U.S. PATENT DOCUMENTS

| | | | | | |
|---|---|---|---|---|---|
| 5,026,400 | A | * | 6/1991 | Holland | ............... C11D 3/3715 |
| | | | | | 510/528 |
| 5,110,506 | A | * | 5/1992 | Ciallella | ............... C11D 3/0036 |
| | | | | | 510/400 |
| 10,323,214 | B2 | * | 6/2019 | Cermenati | ............... C11D 1/83 |
| 2008/0274943 | A1 | * | 11/2008 | Karthauser | .......... C11D 1/8255 |
| | | | | | 568/678 |

FOREIGN PATENT DOCUMENTS

| | | | | | |
|---|---|---|---|---|---|
| EP | 544492 | * | 6/1993 | ............. C11D 17/06 |
| EP | 0544492 A1 | | 6/1993 | |
| EP | 3263687 | * | 1/2018 | ............... C11D 3/36 |
| JP | H03188195 A | | 8/1991 | |

OTHER PUBLICATIONS

Michael F. Cox, "The Effect of Peaking the Ethylene Oxide Distribution on the Performance of Alcohol Ethoxylates and Ether Sulfates", vol. 67, Sep. 1990, pp. 599-604.*
Extended EP Search Report and Written Opinion for EP20199508.1, dated Mar. 3, 2021, 8 pages.
PCT Search Report and Written Opinion for PCT/US2021/052790 dated Jan. 7, 2022, 14 pages.
K. Lee Matheson et al, "Peaked Distribution Ethoxylates-Their Preparation Characterization and Performance Evaluation" vol. 63, Mar. 1986, pp. 365-370.
M. Grant-Huyser et al. "Ethoxylation of Detergent-Range Oxo Alcohols Derived from Fischer—Tropsch a-Olefins" vol. 7, Oct. 2004, pp. 397-407.
NOVEL® Narrow Range Ethoxylates, No Known date, p. 2.

* cited by examiner

*Primary Examiner* — Brian P Mruk

(57) ABSTRACT

The present invention relates generally to narrow range alcohol alkoxylates and derivatives thereof, such as alkyl ether sulfates.

18 Claims, No Drawings

NARROW RANGE ALCOHOL ALKOXYLATES AND DERIVATIVES THEREOF

FIELD OF THE INVENTION

The present invention relates generally to narrow range alcohol ethoxylates.

BACKGROUND OF THE INVENTION

Alcohol alkoxylates and derivatives thereof, such as alkyl ethoxy sulfates (or alcohol ethoxy sulfates (AES)), find utility in a wide variety of applications, e.g., surfactants for use in detergents. The general reaction of alcohols and ethylene oxide to form ethoxylated alcohols or ethylene oxide adducts, has long been known and practiced on a commercial scale. For example, these ethylene oxide adducts have been used as detergents and cleaning agents, domestic and industrial laundry detergents, detergent builders, polishes, sanitizers, and dry cleaning materials.

Much literature is available in the general area of alkoxylation of alcohols. Many references are also available relating to the catalytic ability of various materials, and the mechanism and kinetics of these reactions. Generally, an alkoxylation reaction involving a compound having an active hydrogen, e.g., alcohol, is conducted by the condensation of an alkylene oxide using a suitable catalyst. Both basic, e.g., KOH, and acidic catalysts, e.g., $BF_3$, are known for use in alkoxylating alcohols. Alkoxylation of alcohols, however, produces a distribution of various adducts (homologs), not a pure compound. For example, in surfactant applications, an adduct with too few ethylene oxide molecules may not be effective because of poor solubility, while an adduct with too many ethylene oxide molecules may likewise be undesirable because surface tension reduction per unit mass decreases drastically with increasing molecular weight. Thus, there is a need for alkoxylates with a narrow distribution in the selected mole adduct range for the particular use of the material.

Known acid catalyzed reactions, such as $BF_3$, produce narrow range (peaked) alcohol alkoxylates, but these catalysts produce undesirable side products that must be separated and removed prior to use. Base catalysts normally do not produce the level of by-products which acidic catalysts do, but provide a much broader distribution of alkoxylation adducts. Therefore, it would be desirable to provide alcohol alkoxylates with a narrow distribution of the preferred mole adducts, which are produced by a catalyst system that does not produce undesirable by-products.

SUMMARY OF THE INVENTION

The present disclosure attempts to solve one more of the needs by providing a composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 4-14, wherein less than about 20% by weight of the alcohol ethoxylate are ethoxylates having n<8.

The present disclosure further provides a composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 4-14, wherein the composition comprises between about 35% by weight and about 75% by weight of the alcohol ethoxylates are ethoxylates having n=8-10.

The present disclosure further provides a composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 6-10, wherein less than about 20% by weight of the alcohol ethoxylate are ethoxylates having n<8 and wherein between about 10% by weight and about 20% by weight of the alcohol ethoxylates are ethoxylates having n=8.

DETAILED DESCRIPTION OF THE INVENTION

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein in reference to formula (I), the term "average value of n" refers to the average moles of ethylene oxide, which is the same as the average degree of ethoxylation. The average n may be an integer or a fraction.

As used herein, the articles including "the," "a" and "an" when used in a claim or in the specification, are understood to mean one or more of what is claimed or described.

As used herein, the terms "include," "includes" and "including" are meant to be non-limiting.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the detergent composition unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Narrow Range Alcohol Ethoxylate

The alcohol ethoxylates disclosed herein have the following general formula (I):

(I)

where R is selected from a saturated or unsaturated, linear or branched, $C_8$-$C_{20}$ alkyl group and where greater than 90% of n is $0 \le n \le 15$.

The alcohol ethoxylates described herein are typically not single compounds as suggested by their general formula (I), but rather, they comprise a mixture of several homologs having varied polyalkylene oxide chain length and molecular weight. Among the homologs, those with the number of total alkylene oxide units per mole of alcohol closer to the most prevalent alkylene oxide adduct are desirable; homologs whose number of total alkylene oxide units is much lower or much higher than the most prevalent alkylene oxide adduct are less desirable. In other words, a "narrow range" or "peaked" alkoxylated alcohol composition is desirable. A "narrow range" or "peaked" alkoxylated alcohol composition refers to an alkoxylated alcohol composition having a narrow distribution of alkylene oxide addition moles.

A "narrow range" or "peaked" alkoxylated alcohol composition may be desirable for a selected application. Homologs in the selected target distribution range may have the proper lipophilic-hydrophilic balance for a selected application. For example, in the case of an ethoxylated alcohol product comprising an average ratio of 5 ethylene oxide (EO) units per molecule, homologs having a desired lipophilic-hydrophilic balance may range from 2EO to 9EO. Homologs with shorter EO chain length (<2EO) or longer EO chain length (>9EO) may not be desirable for the applications for which a=5 EO/alcohol ratio surfactant is ordinarily selected, since such longer and shorter homologs are either too lipophilic or too hydrophilic for the applications utilizing this product. Therefore, it is advantageous to develop an alkoxylated alcohol having a peaked distribution.

The narrow range alkoxylated alcohol compositions of the disclosure may have an average degree of ethoxylation ranging from about 0 to about 15, such as, for example, ranging from about 4 to about 14, from about 5-10, from about 8-11, and from about 6-9. The narrow range alkoxylated alcohol compositions of the disclosure may have an average degree of ethoxylation of 10. The narrow range alkoxylated alcohol compositions of the disclosure may have an average degree of ethoxylation of 9. The narrow range alkoxylated alcohol compositions of the disclosure may have an average degree of ethoxylation of 5.

The present disclosure attempts to solve one more of the needs by providing a composition comprising an alcohol ethoxylate of formula (I):

(I)

where R is selected from a saturated or unsaturated, linear or branched, $C_8$-$C_{20}$ alkyl group, where greater than 90% of n is $0 \le n \le 15$, and where the average value of n between about 6 to about 10, where less than about 10% by weight of the alcohol ethoxylate are ethoxylates having n<7 and between 10% and about 20% by weight of the alcohol ethoxylate are ethoxylates having n=8.

The composition may comprise an average value of n of about 10. The composition may have the following ranges for each of the following n:

N=0 of up to 5%, each of n=1, 2, 3, 4, 5 of up to 2%, n=6 of up to 4%, n=7 of up to 10%, n=8 of between 12% and 20%, n=9 of between 15% and 25%, n=10 of between 15% to 30%, n=11 of between 10% and 20%, n=12 of up to 10%, and n>12 at up to 10%. The composition may have n=9 to 10 of between 30% and 70%. The composition may have greater than 50% of its composition made up of n=8 to 11.

The ranges described above are exemplified in Table 1. As shown below in Table 1, samples were analyzed by LCMS ESI (−) after derivatization with DMF-$SO_3$ complex as well as by LCMS ESI (+). % Relative abundances are listed below in the table. Percent Relative Abundance is the weighted average of each ethoxymer relative to the total abundance of all ethoxymers in the sample.

| Moles of EO | Alfonic 1214-9 | Novel 1214-9 |
|---|---|---|
| 0 | 3.14% | 2.33% |
| 1 | 1.26% | 0% |
| 2 | 1.55% | 0% |
| 3 | 2.20% | 0% |
| 4 | 3.08% | 0.39% |
| 5 | 4% | 0.940% |
| 6 | 5.21% | 2.93% |
| 7 | 6.58% | 7.90% |
| 8 | 8.10% | 15.96% |
| 9 | 9.41% | 21.56% |
| 10 | 9.78% | 21.27% |
| 11 | 9.51% | 15.19% |
| 12 | 8.58% | 7.64% |
| 13 | 7.35% | 2.84% |
| 14 | 5.98% | 0.88% |
| 15 | 4.65% | 0.18% |
| 16 | 3.46% | 0% |
| 17 | 2.48% | 0% |
| 18 | 1.74% | 0% |
| 19 | 1.17% | 0% |
| 20 | 0.75% | 0% |

Please note that LCMS-ESI (+) is not sensitive to ethoxymers of less than 3 moles, nor free alcohol. In addition, ethoxymers between 3-5 moles are underrepresented. Typically, if the average distribution of EO is greater than 7 moles of EO, the distribution is not greatly affected by this limit of sensitivity. Additionally, LCMS-ESI (−) can underrepresent heavier ethoxymers when the distribution is very wide, as in ALFONIC samples. For this reason, the ALFONIC sample was analyzed in both +/− modes and the average was taken.

Applicants have surprisingly found that by having a peak curve at n=9-10, the resulting surfactant exhibits improved stain cleaning abilities. This is evidenced in the tables portion of the specification.

The present disclosure also relates to derivatives of narrow range alcohol alkoxylates. There are a number of suitable derivatives of narrow range alcohol alkoxylates. The narrow range molar distribution of the alcohol ethoxylate is maintained in the various derivatives, such as the alcohol ethoxy sulfate. Various processes of sulfating are well known in the art.

The compositions described herein may further comprise (in addition to the alcohol ethoxylate or its sulfated derivative) residual alkoxylation catalyst, which may be considered residue from the reaction or an impurity.

The composition(s) of the disclosure may further comprise (in addition to the alcohol ethoxylate or its sulfated derivative) various impurities or by-products of the alkoxylation reaction. The impurities may vary depending on the catalyst used and the conditions of the reaction. Impurities include alkyl ethers, e.g., dialkyl ethers, such as, didodecyl ether, glycols, e.g., diethylene glycol, triethylene glycol, pentaethylene glycol, other polyethylene glycols, ethoxylated sulfonates (when DDBSA is used as catalyst).

The composition(s) of the disclosure may comprise from about 0.01% to about 4%, or about 0.1% to about 4%, or about 1% to about 4%, by weight of the composition of an impurity selected from the group consisting of alkyl ether, and glycol.

Catalyst and Process of Making Narrow Range Alcohol Alkoxylates

The alkoxylation catalysts described herein allow for the preparation of alcohol alkoxylates having a narrow distribution of alkylene oxide addition moles. It is believed that, in a conventional base-catalyzed alkoxylation reaction, for example, a KOH-catalyzed alcohol ethoxylation reaction, there is a tendency for ethylene oxide to react with alcohol ethoxylate conjugates (alcohol ethoxylate conjugates are more acidic), rather than to react with unreacted alcohol conjugates, thereby yielding a broad range distribution having greater percentages of free alcohol and high-degree ethoxylated alcohols.

The alkoxylation catalysts described herein have a number of advantages for commercial manufacturing compared with known catalysts that provide narrow distribution alkoxylates. The alkoxylation catalysts described herein comprise conventionally used, low-cost raw materials, and the catalysts may be readily prepared. The alkoxylation catalysts described herein are also stable and, therefore, readily handled. Also, the reaction rate, using the alkoxylation catalysts described herein, is similar to previously used alkaline catalysts and suitable for commercial production.

The alkoxylation catalysts described herein are suitable for alkoxylating natural or synthetic, linear or branched, saturated or unsaturated, C8-20 alcohols, alkyl phenols, polyols, etc. having 4-22 carbon atoms. Suitable alcohols include pure linear materials (naturals), lightly branched in C2 position (Neodols®), lightly random-branched (Safols®), highly branched in C2 position (Isalchem®), and highly branched mid-chain materials (HSA). Suitable synthetic alcohols include those sold by Shell Chemical Company under the trademark Neodol®, including Neodol® 25, Neodol® 23, Neodol® 45 and Neodol® 5. Suitable natural alcohols include C1214. In addition, known reaction procedures, reaction conditions, and reactors for alkylene oxides may be used with the alkoxylation catalyst described herein.

The alkoxylation processes described herein may also be run in a series, initially using the acid catalyst described herein and then using a conventional, known catalyst, such as KOH, to yield alkoxylates having a distribution of alkylene oxide addition moles that is narrower than that produced by KOH catalyst alone but broader than that produced by the catalysts of the invention alone. Running the alkoxylation process in series may be particularly useful for higher ethoxylation degree targets, e.g., EO4, EO5, EO6.

The alkoxylation reaction itself may be performed in a single pot or in a continuous process. The ethylene oxide (EO) may initially be reacted with the catalyst, which activates EO to nucleophilic attack. Continuous plant processes with suitable residence time may be used.

The alkoxylation processes disclosed herein may be used to produce alcohol ethoxylates of varying degrees of ethoxylation, including the EO1, EO2, and EO3 targets that are specifically called out. The alkoxylation processes disclosed herein may be also be used to produce other alcohol alkoxylates, e.g., propoxylated alcohol, of varying degrees of alkoxylation.

A suitable method for preparing an ethoxylated alcohol as disclosed herein includes the steps of: i) reacting an excess (for example, from about 0% to about 5% excess) of ethylene oxide with a linear or branched, $C_8$-$C_{20}$ alcohol for stoichiometric target mole ratio of ethylene oxide, in the presence of about 1% to about 10% of a Novel or G2 catalyst.

Applications and Uses

Narrow range alkoxylated alcohols are desirable in a number of applications, particularly in surfactant applications. Narrow range alkoxylate alcohols may be used directly as nonionic surfactants. The narrow range ethoxylate surfactant has numerous uses, including in cleaning compositions or detergents, e.g., laundry detergents.

The narrow range alkoxylated alcohols of the disclosure and the derivatives thereof may be used in detergents at various concentrations. Such detergents may also contain adjuncts. Suitable adjuncts may be selected from the group consisting of a builder, an organic polymeric compound, an enzyme, an enzyme stabilizer, a bleach system, a brightener, a hueing agent, a chelating agent, a suds suppressor, a conditioning agent, a humectant, a perfume, a filler or carrier, an alkalinity system, a pH control system, and a buffer, and mixtures thereof Other Components:

The narrow range alkoxylated alcohols of the disclosure and the derivatives thereof may be used in detergents at various concentrations.

Surfactant

The detergent composition may comprise additional surfactants include anionic surfactants, non-ionic surfactant, cationic surfactants, zwitterionic surfactants and amphoteric surfactants and mixtures thereof. Suitable surfactants may be linear or branched, substituted or un-substituted, and may be derived from petrochemical material or biomaterial. Preferred surfactant systems comprise both anionic and nonionic surfactant, preferably in weight ratios from 90:1 to 1:90. In some instances a weight ratio of anionic to nonionic surfactant of at least 1:1 is preferred. However, a ratio below 10:1 may be preferred. When present, the total surfactant level is preferably from 0.1% to 60%, from 1% to 50% or even from 5% to 40% by weight of the subject composition.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C8-C22 alkyl, or acyl group. Such surfactants are employed in the form of water-soluble salts and the salt-forming cation usually is selected from sodium, potassium, ammonium, magnesium and mono-, with the sodium cation being the usual one chosen.

Anionic surfactants and adjunct anionic cosurfactants, may exist in an acid form, and said acid form may be neutralized to form a surfactant salt which is desirable for use in the present detergent compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, oligoamines, or alkanolamines. Alkanolamines are preferred. Suitable non-limiting examples including monoethanolamine, diethanol amine, triethanol amine, and other linear or branched alkanolamines known in the art; for example, highly preferred alkanolamines include 2-amino-1-propanol, 1-aminopropanol, monoisopropanol amine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Suitable sulfonate surfactants include methyl ester sulfonates, alpha olefin sulfonates, alkyl benzene sulfonates, especially alkyl benzene sulfonates, preferably $C_{10-13}$ alkyl benzene sulfonate, more preferably C12 alkyl benzene sulfonate. Suitable alkyl benzene sulfonate (LAS) is obtainable, preferably obtained, by sulfonating commercially available linear alkyl benzene (LAB). Suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulfonate that is obtained by DETAL catalyzed process, DETAL-PLUS catalyzed process, although other synthesis routes, such as HF, and other alkylation catalysts such as zeolites ZSM-4, ZSM-12, ZSM-20, ZSM-35, ZSM-48, ZSM-50, MCM-22, TMA offretite, TEA mordenite, mordenite, REY and zeolite Beta may also be suitable. In one aspect a magnesium salt of LAS is used. Preferably, the composition may contain from about 0.5% to about 30%, by weight of the laundry composition, of an HLAS surfactant selected from alkyl benzene sulfonic acids, alkali metal or amine salts of C10-16 alkyl benzene sulfonic acids, wherein the HLAS surfactant comprises greater than 50% C12, preferably greater than 60%, preferably greater than 70% C12, more preferably greater than 75%

Suitable sulfate surfactants include alkyl sulfate, preferably C8-18 alkyl sulfate, or predominantly C12/14 alkyl sulfate.

The alkyl sulfate, and alkyl benzene sulfonates may be linear or branched, including 2-alkyl substituted or mid chain branched type, substituted or un-substituted, and may be derived from petrochemical material or biomaterial. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the detergent of the invention. Most preferably the branched sulfated anionic surfactant is selected from alkyl sulfates, and mixtures thereof.

Other suitable anionic surfactants include the class of glycolipids, such as sophorolipids and rhamnolipids and amino acid-based surfactants, e.g., acyl glycinates, acyl sarcosinates, acyl glutamates, and acyl taurates. The rhamnolipids may have a single rhamnose sugar ring or two rhamnose sugar rings.

Non-Ionic Surfactant:

Suitable non-ionic surfactants are selected from the group consisting of: $C_8$-$C_{18}$ alkyl ethoxylates, such as, NEODOL® non-ionic surfactants from Shell; alkyl polysaccharides, preferably alkylpolyglycosides and alkyl polypentosides; fatty acid methyl ester ethoxylates; polyhydroxy fatty acid amides; ether capped poly(oxyalkylated) alcohol surfactants; alkyl and alkenyl furan sulfonates and alkyl and alkenyl furan sulfates, and mixtures thereof.

Suitable non-ionic surfactants are alkyl polyglucosides and/or an alkyl alkoxylated alcohol.

Suitable non-ionic surfactants include alkyl alkoxylated alcohols, preferably $C_{8-18}$ alkyl alkoxylated alcohol, preferably a $C_{8-18}$ alkyl ethoxylated alcohol, preferably the alkyl alkoxylated alcohol has an average degree of alkoxylation of from 1 to 50, preferably from 1 to 30, or from 1 to 20, or from 1 to 10, preferably the alkyl alkoxylated alcohol is a $C_{8-18}$ alkyl ethoxylated alcohol having an average degree of ethoxylation of from 1 to 10, preferably from 1 to 7, more preferably from 1 to 5 and most preferably from 3 to 7. In one aspect, the alkyl alkoxylated alcohol is a $C_{12-15}$ alkyl ethoxylated alcohol having an average degree of ethoxylation of from 7 to 10. The alkyl alkoxylated alcohol can be linear or branched and substituted or un-substituted. Suitable nonionic surfactants include those with the trade name Lutensol® from BASF. The alkyl alkoxylated sulfate may have a broad alkoxy distribution for example Alfonic 1214-9 Ethoxylate or a peaked alkoxy distribution for example Novel 1214-9 both commercially available from Sasol Cationic Surfactant:

Suitable cationic surfactants include alkyl pyridinium compounds, alkyl quaternary ammonium compounds, alkyl quaternary phosphonium compounds, alkyl ternary sulfonium compounds, and mixtures thereof.

Preferred cationic surfactants are quaternary ammonium compounds having the general formula:

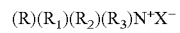

$(R)(R_1)(R_2)(R_3)N^+X^-$ wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, preferred anions include: halides, preferably chloride; sulphate; and sulfonate.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines, imidazoline quat materials and quaternary ammonium surfactants, preferably N, N-bis (stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methyl sulfate; 1, 2 di (stearoyl-oxy) 3 trimethyl ammonium propane chloride dialkylene dimethyl ammonium salts such as dicanoladimethylammonium chloride, di(hard)tallow dimethyl ammonium chloride dicanoladimethylammonium methyl sulfate; 1-methyl-1-stearoylamidoethyl-2-stearoylimidazolinium methyl sulfate; 1-tallowylamidoethyl-2-tallowylimidazoline; N,N"-dialkyl diethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Amphoteric and Zwitterionic Surfactant

Suitable amphoteric or zwitterionic surfactants include amine oxides, and/or betaines. Preferred amine oxides are alkyl dimethyl amine oxide or alkyl amidopropyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 $C_{8-18}$ alkyl moiety and 2 R2 and R3 moieties selected from the group consisting of C1-3 alkyl groups and C1-3 hydroxyalkyl groups. Preferably amine oxide is characterized by the formula R1-N(R2)(R3) O wherein R1 is a $C_{8-18}$ alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides.

It has been surprisingly found that one can reap the grease cleaning benefits of amine oxide while controlling the level of suds in the wash cycle without the use of silicone suds suppressors. As shown in Tables 1-5, it has been surprisingly found that by utilizing selective ratios of Fatty Acid (FA) to Amine Oxide (AO), one can create a cleaning composition that exhibits 'best in class' cleaning performance, cycle times, and water usage without the use of AES surfactants and silicone suds suppressors.

Other suitable surfactants include betaines, such as alkyl betaines, alkylamidobetaine, amidazoliniumbetaine, sulfobetaine (sultaines) as well as phosphobetaines.

Shading Dye

Fabric shading can be accomplished through application of any suitable ingredient as known in the art. Preferred fabric shading agents include fabric shading dyes, leuco dyes, pigments and mixtures thereof.

Fabric shading leading in some cases to whiteness improvements can be accomplished through application of leuco dyes via use of a single compound or a leuco composition comprising at least one leuco compound comprising any suitable leuco moiety. In one aspect, the leuco moiety is selected from the group consisting diarylmethane leuco moieties, triarylmethane leuco moieties, oxazine moieties, thiazine moieties, hydroquinone moieties, and arylaminophenol moieties. The leuco compound may comprise a leuco moiety and an alkyleneoxy moiety covalently bound to the leuco moiety, wherein the alkyleneoxy moiety comprises at least one ethylene oxide group, preferably the alkylene oxide moiety also comprises at least one propylene oxide group. In one aspect, preferred leuco compounds include those conforming to the structure of Formula (CVIII),

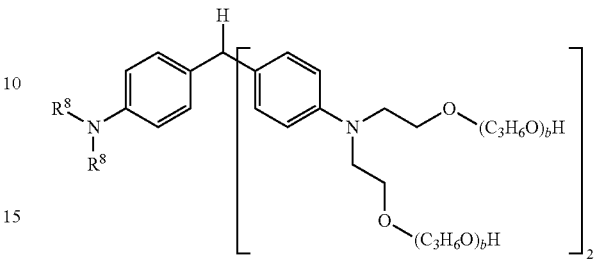

(CVIII)

wherein $R^8$ is H or $CH_3$ and each index b is independently on average about 1 to 2. Other suitable leuco dyes are disclosed in U.S. Pat. Nos. 10,377,976, 10,377,977, 10,351,709, 10,385,294, 10,472,595, 10,479,961, 10,501,633, 10,577,570, 10,590,275, 10,633,618, 10,647,854, and 10,676,699, incorporated in their entirety herein by reference.

The composition may comprise an additional fabric shading agent. Suitable fabric shading agents include dyes, dye-clay conjugates, and pigments. Suitable dyes include small molecule dyes and polymeric dyes. Suitable small molecule dyes include small molecule dyes selected from the group consisting of dyes falling into the Color Index (C. I.) classifications of Direct Blue, Direct Red, Direct Violet, Acid Blue, Acid Red, Acid Violet, Basic Blue, Basic Violet and Basic Red, or mixtures thereof. Preferred dyes include alkoxylated azothiophenes, Solvent Violet 13, Acid Violet 50 and Direct Violet 9.

Leuco Colorant Diluent

Another class of ingredients in the leuco colorants composition may be a diluent and/or solvent. The purpose of the diluent and/or solvent is often, but not limited to, improving fluidity and/or reducing the viscosity of the leuco colorant. Although water is often the preferred diluent and/or solvent given its low cost and non-toxicity, other solvent may also be used as well. The preferred solvent is one having low cost and low hazards. Examples of suitable solvents include, but are not limited to, ethylene glycol, propylene glycol, glycerin, alkoxylated polymers such as polyethylene glycol, polypropylene glycol, copolymers of ethylene oxide and propylene oxide, Tween 20®, Tween 40®, Tween 80®, and the like, and combinations thereof. Among the polymers, the ethylene oxide and propylene oxide copolymers may be preferred. These polymers often feature a cloud point with water, which can help the product separated from the water to remove the undesirable water-soluble impurities. Examples of ethylene oxide and propylene oxide copolymers include but not limited to the PLURONIC series polymers by BASF and TERGITOL™ series polymer and by Dow. When the leuco colorant composition is incorporated into the laundry care composition, these polymers may also act as a non-ionic surfactant.

Fabric shading can be accomplished through application of any suitable ingredient as known in the art. Preferred fabric shading agents include fabric shading dyes, leuco dyes, pigments and mixtures thereof.

Fabric shading leading in some cases to whiteness improvements can be accomplished through application of leuco dyes via use of a single compound or a leuco composition comprising at least one leuco compound comprising any suitable leuco moiety. In one aspect, the leuco moiety is selected from the group consisting diarylmethane leuco moieties, triarylmethane leuco moieties, oxazine moieties, thiazine moieties, hydroquinone moieties, and arylaminophenol moieties. The leuco compound may comprise a leuco moiety and an alkyleneoxy moiety covalently bound to the leuco moiety, wherein the alkyleneoxy moiety comprises at least one ethylene oxide group, preferably the alkylene oxide moiety also comprises at least one propylene oxide group. In one aspect, preferred leuco compounds include those conforming to the structure of Formula (CVIII),

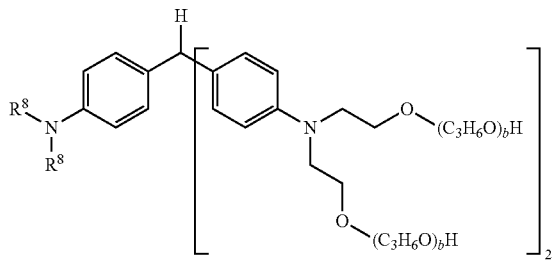

wherein $R^8$ is H or $CH_3$ and each index b is independently on average about 1 to 2. Other suitable leuco dyes are disclosed in U.S. Pat. Nos. 10,377,976, 10,377,977, 10,351,709, 10,385,294, 10,472,595, 10,479,961, 10,501,633, 10,577,570, 10,590,275, 10,633,618, 10,647,854, and 10,676,699, incorporated in their entirety herein by reference.

The laundry care compositions described herein may also include one or more of the following non-limiting list of ingredients: fabric care benefit agent; detersive enzyme; deposition aid; rheology modifier; builder; chelant; bleach; bleaching agent; bleach precursor; bleach booster; bleach catalyst; perfume and/or perfume microcapsules; perfume loaded zeolite; starch encapsulated accord; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; cationic starches; scum dispersants; substantive dyes; colorants; opacifier; antioxidant; hydrotropes such as toluene sulfonates, cumene sulfonates and naphthalene sulfonates; color speckles; colored beads, spheres or extrudates; clay softening agents; anti-bacterial agents. Additionally, or alternatively, the compositions may comprise surfactants, quaternary ammonium compounds, and/or solvent systems. Quaternary ammonium compounds may be present in fabric enhancer compositions, such as fabric softeners, and comprise quaternary ammonium cations that are positively charged polyatomic ions of the structure $NR_4^+$, where R is an alkyl group or an aryl group.
Encapsulates.

The composition may comprise an encapsulated material. In one aspect, an encapsulate comprising a core, a shell having an inner and outer surface, said shell encapsulating said core. The core may comprise any laundry care adjunct, though typically the core may comprise material selected from the group consisting of perfumes; brighteners; hueing dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinyl alcohols, optionally containing other co-monomers; polystyrenes; polyisoprenes; polycarbonates; polyesters; polyacrylates; aminoplasts, in one aspect said aminoplasts may comprise a polyurea, polyurethane, and/or polyurea urethane, in one aspect said polyurea may comprise polyoxymethylene urea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.
Perfume.

Preferred compositions of the invention comprise perfume. Typically, the composition comprises a perfume that comprises one or more perfume raw materials, selected from the group as described in WO08/87497. However, any perfume useful in a laundry care composition may be used.
Polymers.

The composition may comprise one or more polymers. Examples are optionally modified carboxymethylcellulose, modified polyglucans, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers. Such polymers have balanced hydrophilic and hydrophobic properties such that they remove grease particles from fabrics and surfaces.
Zwitterionic Polyamine:

The composition may comprise a zwitterionic polyamine that is a modified hexamethylenediamine. The modification of the hexamethylenediamine includes: (1) one or two alkoxylation modifications per nitrogen atom of the hexamethylenediamine. The alkoxylation modification consisting of the replacement of a hydrogen atom on the nitrogen of the hexamethylenediamine by a (poly)alkoxylene chain having an average of about 1 to about 40 alkoxy moieties per modification, wherein the terminal alkoxy moiety of the alkoxylene chain is capped with hydrogen, a C1-C4 alkyl, sulfates, carbonates, or mixtures thereof (2) a substitution of one C1-C4 alkyl moiety and one or two alkoxylation modifications per nitrogen atom of the hexamethylenediamine. The alkoxylation modification consisting of the replacement of a hydrogen atom by a (poly)alkoxylene chain having an average of about 1 to about 40 alkoxy moieties per modification wherein the terminal alkoxy moiety of the alkoxylene chain is capped with hydrogen, a C1-C4 alkyl or mixtures thereof; or (3) a combination thereof
Amphiphilic Graft Copolymer:

Other suitable polymers include amphiphilic graft copolymers. Preferred amphiphilic graft co-polymer(s) comprise (i) polyethylene glycol backbone; and (ii) and at least one pendant moiety selected from polyvinyl acetate, polyvinyl alcohol and mixtures thereof. An example of amphiphilic graft co-polymer is Sokalan HP22, supplied from BASF. Other suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably about 6000 and the weight ratio of the polyethylene oxide to polyvinyl acetate is about 40 to 60 and less than or equal to 1 grafting point per 50 ethylene oxide units. Typically, these are incorporated into the compositions of the invention in amounts from 0.005 to 10 wt %, more usually from 0.05 to 8 wt %.

Soil Release Polymers:

The composition may comprise one or more soil release polymers. Examples include soil release polymers having a structure as defined by one of the following Formula (VI), (VII) or (VIII):

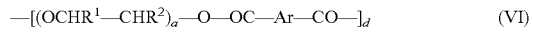  (VI)

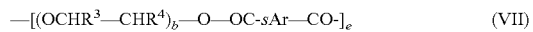  (VII)

  (VIII)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Na, Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN260, SRN300 and SRN325 supplied by Clariant. Other suitable soil release polymers are Marloquest polymers, such as Marloquest SL supplied by Sasol. Known polymeric soil release agents, hereinafter "SRA" or "SRA's", can optionally be employed in the present detergent compositions. If utilized, SRA's will generally comprise from 0.01% to 10.0%, typically from 0.1% to 5%, preferably from 0.2% to 3.0% by weight, of the composition.

SRA's can include, for example, a variety of charged, e.g., anionic or even cationic (see U.S. Pat. No. 4,956,447), as well as noncharged monomer units and structures may be linear, branched or even star-shaped. Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044.

Carboxylate Polymer:

The composition may comprise a carboxylate polymer, such as a maleate/acrylate random copolymer or polyacrylate homopolymer. Suitable carboxylate polymers include: polyacrylate homopolymers having a molecular weight of from 4,000 Da to 9,000 Da; maleate/acrylate random copolymers having a molecular weight of from 50,000 Da to 100,000 Da, or from 60,000 Da to 80,000 Da.

Alternatively, these materials may comprise polyacrylates having one ethoxy side-chain per every 7-8 acrylate units. The side-chains are of the formula —$(CH_2CH_2O)_m(CH_2)_n$ $CH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Alkoxylated Polyamine-Based Polymers:

The composition may comprise alkoxylated polyamines. Such materials include but are not limited to ethoxylated polyethyleneimine, ethoxylated hexamethylene diamine, and sulfated versions thereof. Polypropoxylated derivatives are also included. A wide variety of amines and polyalkyleneimines can be alkoxylated to various degrees, and optionally further modified to provide the abovementioned benefits. A useful example is 600 g/mol polyethyleneimine core ethoxylated to 20 EO groups per NH. A preferred ethoxylated polyethyleneimine is PE-20 available from BASF.

Cellulosic Polymer:

Cellulosic polymers may be used according to the invention. Suitable cellulosic polymers are selected from alkyl cellulose, alkyl alkoxyalkyl cellulose, carboxyalkyl cellulose, alkyl carboxyalkyl cellulose, sulphoalkyl cellulose, more preferably selected from carboxymethyl cellulose, methyl cellulose, methyl hydroxyethyl cellulose, methyl carboxymethyl cellulose, and mixtures thereof. Suitable carboxymethyl celluloses have a degree of carboxymethyl substitution from 0.5 to 0.9 and a molecular weight from 100,000 Da to 300,000 Da. Suitable carboxymethyl celluloses have a degree of substitution greater than 0.65 and a degree of blockiness greater than 0.45, e.g. as described in WO09/154933.

Cationic Polymers:

Cationic polymers may also be used according to the invention. Suitable cationic polymers will have cationic charge densities of at least 0.5 meq/gm, in another embodiment at least 0.9 meq/gm, in another embodiment at least 1.2 meq/gm, in yet another embodiment at least 1.5 meq/gm, but in one embodiment also less than 7 meq/gm, and in another embodiment less than 5 meq/gm, at the pH of intended use of the composition, which pH will generally range from pH 3 to pH 9, in one embodiment between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, in one embodiment between 50,000 and 5 million, and in another embodiment between 100,000 and 3 million. Suitable cationic polymers are described in U.S. Pat. Nos. 3,962,418; 3,958,581; and U.S. Publication No. 2007/0207109A1.

Dye Transfer Inhibitor (DTI).

The composition may comprise one or more dye transfer inhibiting agents. In one embodiment of the invention the inventors have surprisingly found that compositions comprising polymeric dye transfer inhibiting agents in addition to the specified dye give improved performance. This is surprising because these polymers prevent dye deposition. Suitable dye transfer inhibitors include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Suitable examples include PVP-K15, PVP-K30, ChromaBond S-400, ChromaBond S-403E and Chromabond S-100 from Ashland Aqualon, and Sokalan HP165, Sokalan HP50, Sokalan HP53, Sokalan HP59, Sokalan® HP 56K, Sokalan® HP 66 from BASF. The dye control agent may be selected from (i) a sulfonated phenol/formaldehyde polymer; (ii) a urea derivative; (iii) polymers of ethylenically unsaturated monomers, where the polymers are molecularly imprinted with dye; (iv) fibers consisting of water-insoluble polyamide, wherein the fibers have an average diameter of not more than about 2 µm; (v) a polymer obtainable from polymerizing benzoxazine monomer compounds; and (vi) combinations thereof. Other suitable DTIs are as described in WO2012/004134. When present in a subject composition, the dye transfer inhibiting agents may be present at levels from about 0.0001% to about 10%, from about 0.01% to about 5% or even from about 0.1% to about 3% by weight of the composition.

Other Water-Soluble Polymers:

Examples of water soluble polymers include but are not limited to polyvinyl alcohols (PVA), modified PVAs; polyvinyl pyrrolidone; PVA copolymers such as PVA/polyvinyl pyrrolidone and PVA/polyvinyl amine; partially hydrolyzed polyvinyl acetate; polyalkylene oxides such as polyethylene oxide; polyethylene glycols; acrylamide; acrylic acid; cellulose, alkyl cellulosics such as methyl cellulose, ethyl cellulose and propyl cellulose; cellulose ethers; cellulose esters; cellulose amides; polyvinyl acetates; polycarboxylic acids and salts; polyaminoacids or peptides; polyamides; polyacrylamide; copolymers of maleic/acrylic acids; polysaccharides including starch, modified starch; gelatin; alginates; xyloglucans, other hemicellulosic polysaccharides including xylan, glucuronoxylan, arabinoxylan, mannan, glucomannan and galactoglucomannan; and natural gums such as pectin, xanthan, and carrageenan, locus bean, arabic, tragacanth; and combinations thereof.

Oligoamines:

Non-limiting examples of amines include, but are not limited to, etheramines, cyclic amines, polyamines, oligoamines (e.g., triamines, diamines, pentamines, tetraamines), or combinations thereof. The compositions described herein may comprise an amine selected from the group consisting of oligoamines, etheramines, cyclic amines, and combinations thereof. In some aspects, the amine is not an alkanolamine. In some aspects, the amine is not a polyalkyleneimine.

Examples of suitable oligoamines include Preferably the composition comprises oligoamines. Suitable oligoamines according to the present disclosure may include diethylenetriamine (DETA), 4-methyl diethylenetriamine (4-MeDETA), dipropylenetriamine (DPTA), 5-methyl dipropylenetriamine (5-MeDPTA), triethylenetetraamine (TETA), 4-methyl triethylenetetraamine (4-MeTETA), 4,7-dimethyl triethylenetetraamine (4,7-Me2TETA), 1,1,4,7,7-pentamethyl diethylenetriamine (M5-DETA), tripropylenetetraamine (TPTA), tetraethylenepentaamine (TEPA), tetrapropylenepentaamine (TPPA), pentaethylenehexaamine (PEHA), pentapropylenehexaamine (PPHA), hexaethyleneheptaamine (HEHA), hexapropyleneheptaamine (HPHA), N,N'-Bis(3-aminopropyl)ethylenediamine, 1,1,4,7,7-pentamethyl diethylenetriamine (M5-DETA), dipropylenetriamine (DPTA) or mixtures thereof most preferably diethylenetriamine (DETA). DETA may be preferred due to its low molecular weight and/or relatively low cost to produce.

The oligoamines of the present disclosure may have a molecular weight of between about 100 to about 1200 Da, or from about 100 to about 900 Da, or from about 100 to about 600 Da, or from about 100 to about 400 Da, preferably between about 100 Da and about 250 Da, most preferably between about 100 Da and about 175 Da, or even between about 100 Da and about 150 Da. For purposes of the present disclosure, the molecular weight is determined using the free base form of the oligoamine.

Etheramines:

The cleaning compositions described herein may contain an etheramine. The cleaning compositions may contain from about 0.1% to about 10%, or from about 0.2% to about 5%, or from about 0.5% to about 4%, by weight of the composition, of an etheramine.

The etheramines of the present disclosure may have a weight average molecular weight of less than about grams/mole 1000 grams/mole, or from about 100 to about 800 grams/mole, or from about 200 to about 450 grams/mole, or from about 290 to about 1000 grams/mole, or from about 290 to about 900 grams/mole, or from about 300 to about 700 grams/mole, or from about 300 to about 450 grams/mole. The etheramines of the present invention may have a weight average molecular weight of from about 150, or from about 200, or from about 350, or from about 500 grams/mole, to about 1000, or to about 900, or to about 800 grams/mole.

Enzymes.

Preferably the composition comprises one or more enzymes. Preferred enzymes provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in the composition, the aforementioned additional enzymes may be present at levels from about 0.00001% to about 2%, from about 0.0001% to about 1% or even from about 0.001% to about 0.5% enzyme protein by weight of the composition.

Builders.

Preferably the composition may comprise one or more builders or a builder system. When a builder is used, the composition of the invention will typically comprise at least 1%, from 2% to 60% builder. It may be preferred that the composition comprises low levels of phosphate salt and/or zeolite, for example from 1 to 10 or 5 wt %. The composition may even be substantially free of strong builder; substantially free of strong builder means "no deliberately added" zeolite and/or phosphate. Typical zeolite builders include zeolite A, zeolite P and zeolite MAP. A typical phosphate builder is sodium tri-polyphosphate.

Organic Acid

The detergent comprises one or more organic acids selected from the group consisting of acetic acid, adipic acid, aspartic acid, carboxymethyloxymalonic acid, carboxymethyloxysuccinic acid, citric acid, formic acid, glutaric acid, hydroxyethyliminodiacetic acid, iminodiacetic acid, lactic acid, maleic acid, malic acid, malonic acid, oxydiacetic acid, oxydisuccinic acid, succinic acid, sulfamic acid, tartaric acid, tartaric-disuccinic acid, tartaric-monosuccinic acid, or mixtures thereof.

Preferably, the detergent composition may comprise an organic acid selected from the group consisting of acetic acid, lactic acid, and citric acid.

Chelating Agent.

Preferably the composition comprises chelating agents and/or crystal growth inhibitor. Suitable molecules include copper, iron and/or manganese chelating agents and mixtures thereof. Suitable molecules include hydroxamic acids, aminocarboxylates, aminophosphonates, succinates, salts thereof, and mixtures thereof. Non-limiting examples of suitable chelants for use herein include ethylenediaminetetracetates, N-(hydroxyethyl)ethylenediaminetriacetates, nitrilotriacetates, ethylenediamine tetraprorionates, triethylenetetraaminehexacetates, diethylenetriamine-pentaacetates, ethanoldiglycines, ethylenediaminetetrakis (methylenephosphonates), diethylenetriamine penta(methylene phosphonic acid) (DTPMP), ethylenediamine disuccinate (EDDS), hydroxyethanedimethylenephosphonic acid (HEDP), methylglycinediacetic acid (MGDA), diethylenetriaminepentaacetic acid (DTPA), N,N-Dicarboxymethyl glutamic acid (GLDA) and salts thereof, and mixtures thereof. Other nonlimiting examples of chelants of use in the present invention are found in U.S. Pat. Nos. 7,445,644, 7,585,376 and 2009/0176684A1. Other suitable chelating agents for use herein are the commercial DEQUEST series, and chelants from Monsanto, DuPont, and Nalco, Inc. Yet other suitable chelants include the pyridinyl N Oxide type.

Fluorescent Brightener:

Commercial fluorescent brighteners suitable for the present disclosure can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents.

The fluorescent brightener may be selected from the group consisting of disodium 4,4'-bis{[4-anilino-6-morpholino-s-triazin-2-yl]-amino}-2,2'-stilbenedisulfonate (brightener 15, commercially available under the tradename Tinopal AMS-GX by BASF), disodium 4,4'-bis{[4-anilino-6-(N-2-bis-hydroxyethyl)-s-triazine-2-yl]-amino}-2,2'-stilbenedisulonate (commercially available under the tradename Tinopal UNPA-GX by BASF), disodium 4,4'-bis{[4-anilino-6-(N-2-hydroxyethyl-N-methylamino)-s-triazine-2-yl]-amino}-2,2'-stilbenedisulfonate (commercially available under the tradename Tinopal 5BM-GX by BASF). More preferably, the fluorescent brightener is disodium 4,4'-bis{[4-anilino-6-morpholino-s-triazin-2-yl]-amino}-2,2'-stilbenedisulfonate or 2,2'-([1,1'-Biphenyl]-4,4'-diyldi-2,1-ethenediyl)bis-benzenesulfonic acid disodium salt. The brighteners may be added in particulate form or as a premix with a suitable solvent, for example nonionic surfactant, propanediol.

Enzyme Stabilizers.

The composition may preferably comprise enzyme stabilizers. Any conventional enzyme stabilizer may be used, for example by the presence of water-soluble sources of calcium and/or magnesium ions in the finished fabric and home care products that provide such ions to the enzymes. In case of aqueous compositions comprising protease, a reversible protease inhibitor, such as a boron compound including borate, or preferably 4-formyl phenylboronic acid, phenylboronic acid and derivatives thereof, or compounds such as calcium formate, sodium formate and 1,2-propane diol can be added to further improve stability.

Solvents:

The solvent system in the present compositions can be a solvent system containing water alone or mixtures of organic solvents either without or preferably with water. The compositions may optionally comprise an organic solvent. Suitable organic solvents include $C_{4-14}$ ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-$C_5$ alcohols, linear $C_1$-$C_5$ alcohols, amines, $C_8$-$C_{14}$ alkyl and cycloalkyl hydrocarbons and halohydrocarbons, and mixtures thereof. Preferred organic solvents include 1,2-propanediol, 2,3 butane diol, ethanol, glycerol, ethoxylated glycerol, dipropylene glycol, methyl propane diol and mixtures thereof 2 ethyl hexanol, 3,5,5, trimethyl-1 hexanol, and 2 propyl heptanol. Solvents may be a polyethylene or polypropylene glycol ether of glycerin. Other lower alcohols, C1-C4 alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 1% to about 50%, more usually from about 5% to about 25%, alternatively from about 1% to about 10% by weight of the liquid detergent composition of said organic solvent. These organic solvents may be used in conjunction with water, or they may be used without water Structured Liquids:

In some embodiments of the invention, the composition is in the form of a structured liquid. Such structured liquids can either be internally structured, whereby the structure is formed by primary ingredients (e.g. surfactant material) and/or externally structured by providing a three dimensional matrix structure using secondary ingredients (e.g. polymers, clay and/or silicate material), for use e.g. as thickeners. The composition may comprise a structurant, preferably from 0.01 wt % to 5 wt %, from 0.1 wt % to 2.0 wt % structurant. Examples of suitable structurants are given in US2006/0205631A1, US2005/0203213A1, U.S. Pat. Nos. 7,294,611, 6,855,680. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, hydrogenated castor oil, derivatives of hydrogenated castor oil such as non-ethoxylated derivatives thereof and mixtures thereof, in particular, those selected from the group of hydrogenated castor oil, derivatives of hydrogenated castor oil, microfibullar cellulose, hydroxyfunctional crystalline materials, long chain fatty alcohols, 12-hydroxystearic acids, clays and mixtures thereof. One preferred structurant is described in U.S. Pat. No. 6,855,680 which defines suitable hydroxyfunctional crystalline materials in detail. Preferred is hydrogenated castor oil. Some structurants have a thread-like structuring system having a range of aspect ratios. Another preferred structurant is based on cellulose and may be derived from a number of sources including biomass, wood pulp, citrus fibers and the like.

Conditioning Agents:

Suitable conditioning agents include high melting point fatty compounds. The high melting point fatty compound useful herein has a melting point of 25° C. or higher and is selected from the group consisting of fatty alcohols, fatty acids, fatty alcohol derivatives, fatty acid derivatives, and mixtures thereof. Preferred fatty acid blends may be mixtures enriched or fatty acid mixtures enriched with 2-alkyl fatty acid, preferably 2-methyl octanoic acid. Suitable conditioning agents also include nonionic polymers and conditioning oils, such as hydrocarbon oils, polyolefins, and fatty esters.

Suitable conditioning agents include those conditioning agents characterized generally as silicones (e.g., silicone oils, polyoils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters.

Probiotics:

The composition may comprise probiotics, such as those described in WO2009/043709.

Pearlescent Agent:

Non-limiting examples of pearlescent agents include: mica; titanium dioxide coated mica; bismuth oxychloride; fish scales; mono and diesters of alkylene glycol. The pearlescent agent may be ethyleneglycoldistearate (EGDS).

Opacifier:

In one embodiment, the composition might also comprise an opacifier. As the term is used herein, an "opacifier" is a substance added to a material in order to make the ensuing system opaque. In one preferred embodiment, the opacifier is Acusol, which is available from Dow Chemicals. Acusol opacifiers are provided in liquid form at a certain % solids level. As supplied, the pH of Acusol opacifiers ranges from 2.0 to 5.0 and particle sizes range from 0.17 to 0.45 um. In one preferred embodiment, Acusol OP303B and 301 can be used.

In yet another embodiment, the opacifier may be an inorganic opacifier. Preferably, the inorganic opacifier can be $TiO_2$, ZnO, talc, $CaCO_3$, and combination thereof. The composite opacifier-microsphere material is readily formed with a preselected specific gravity, so that there is little tendency for the material to separate.

Hydrotrope:

The composition may optionally comprise a hydrotrope in an effective amount, i.e. from about 0% to 15%, or about 1% to 10%, or about 3% to about 6%, so that compositions are compatible in water. Suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903.

Anti-Oxidant:

The composition may optionally contain an anti-oxidant present in the composition from about 0.001 to about 2% by weight. Preferably the antioxidant is present at a concentration in the range 0.01 to 0.08% by weight. Mixtures of anti-oxidants may be used.

Anti-oxidants are substances as described in Kirk-Othmer (Vol. 3, page 424) and In Ullmann's Encyclopedia (Vol. 3, page 91).

One class of anti-oxidants used in the present invention is alkylated phenols, having the general formula:

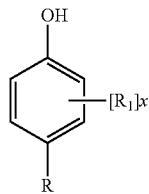

wherein R is $C_1$-$C_{22}$ linear or branched alkyl, preferably methyl or branched $C_3$-$C_6$ alkyl, $C_1$-$C_6$ alkoxy, preferably methoxy; $R_1$ is a $C_3$-$C_6$ branched alkyl, preferably tert-butyl; x is 1 or 2. Hindered phenolic compounds are a preferred type of alkylated phenols having this formula. Examples of such hindered phenol antioxidants may include, but are not limited to: 2,6-bis(1-methylpropyl)phenol; 2,6-bis(1,1-dimethylethyl)-4-methyl-phenol (also known as hydroxy butylated toluene, "BHT"); 2-(1,1-dimethylethyl)-1,4-benzenediol; 2,4-bis(1,1-dimethylethyl)-phenol; 2,6-bis(1,1-dimethylethyl)-phenol; 3,5-bis(1,1-dimethylethyl)-4-hydroxybenzene propanoic acid, methyl ester; 2-(1,1-dimethylethyl)-4-methylphenol; 2-(1,1-dimethylethyl)-4,6-dimethyl-phenol; 3,5-bis(1,1-dimethylethyl)-4-hydroxybenzenepropanoic acid, 1,1'-[2,2-bis[[3-[3,5-bis(1,1-dimethylethyl)-4-hydroxyphenyl]-1-oxopropoxy]methyl]-1,3-propanediyl] ester; 3,5-bis(1,1-dimethylethyl)-4-hydroxybenzenepropanoic acid, octadecyl ester; 2,2'-methylenebis[6-(1,1-dimethylethyl)-4-methylphenol; 2-(1,1-dimethylethyl)-phenol; 2,4,6-tris(1,1-dimethylethyl)-phenol; 4,4'-methylenebis[2,6-bis(1,1-dimethylethyl)-phenol; 4,4',4"-[(2,4,6-trimethyl-1,3,5-benzenetriyl)tris(methylene)]tris[2,6-bis(1,1-dimethylethyl)-phenol]; N,N'-1,6-hexanediylbis[3,5-bis(1,1-dimethylethyl)-4-hydroxybenzenepropanamide; 3,5-bis(1,1-dimethylethyl)-4-hydroxy benzoic acid, hexadecyl ester; P-[[3,5-bis(1,1-dimethylethyl)-4-hydroxyphenyl]methylphosphonic acid, diethyl ester; 1,3,5-tris[[3,5-bis(1,1-dimethylethyl)-4-hydroxyphenyl]methyl]-1,3,5-Triazine-2,4,6(1H,3H,5H)-trione; 3,5-bis(1,1-5 dimethylethyl)-4-hydroxybenzenepropanoic acid, 2-[3-[3,5-bis(1,1-dimethylethyl)-4-hydroxyphenyl]-1-oxopropyl]hydrazide; 3-(1,1-dimethylethyl)-4-hydroxy-5-methylbenzenepropanoic acid, 1,1'-[1,2-ethanediylbis(oxy-2,1-ethanediyl)] ester; 4-[(dimethylamino)methyl]-2,6-bis(1,1-dimethylethyl)phenol; 4-[[4,6-bis(octylthio)-1,3,5-triazin-2-yl]amino]-2,6-bis(1,1-dimethylethyl)phenol; 3,5-bis(1,1-dimethylethyl)-4-hydroxy benzene propanoic acid, 1,1'-(thiodi-2,1-ethanediyl) ester; 3,5-bis(1,1-dimethylethyl)-4-hydroxybenzoic acid, 2,4-bis(1,1-dimethylethyl)phenyl ester; 3,5-bis(1,1-dimethylethyl)-4-hydroxybenzenepropanoic acid, 1,1'-(1,6-hexanediyl)ester; 3-(1,1-dimethylethyl)-4-hydroxy-5-methylbenzenepropanoic acid, 1,1'-[2,4,8,10-tetraoxaspiro[5.5]undecane-3,9-diylbis(2,2-dimethyl-2,1-ethanediyl)] ester; 3-(1,1-dimethylethyl)-b-[3-(1,1-dimethylethyl)-4-hydroxy phenyl]-4-hydroxy-b-methylbenzenepropanoic acid, 1,1'-(1,2-ethanediyl) ester; 2-[[3,5-bis(1,1-dimethylethyl)-4-hydroxyphenyl]methyl]-2-butylpropanedioic acid, 1,3-bis(1,2,2,6,6-pentamethyl-4-piperidinyl) ester; 3,5-bis(1,1-dimethylethyl)-4-hydroxybenzenepropanoic acid, 1-[2-[3-[3,5-bis(1,1-dimethylethyl)-4-hydroxyphenyl]-1-oxopropoxy]ethyl]-2,2,6,6-tetramethyl-4-piperidinyl ester; 3,4-dihydro-2,5,7,8-tetramethyl-2-[(4R, 8R)-4,8,12-trimethyltridecyl]-(2R)-2H-1-benzopyran-6-ol; 2,6-dimethylphenol; 2,3,5-trimethyl-1,4-benzenediol; 2,4,6-trimethylphenol; 2,3,6-trimethylphenol; 4,4'-(1-methylethylidene)-bis[2,6-dimethylphenol]; 1,3,5-tris[[4-(1,1-dimethylethyl)-3-hydroxy-2,6-dimethylphenyl]methyl]-1,3,5-triazine-2,4,6(1H,3H,5H)-trione; 4,4'-methylenebis[2,6-dimethylphenol]; and mixtures thereof.

Preferably, the hindered phenol antioxidant comprises at least one phenolic —OH group having at least one C3-C6 branched alkyl at a position ortho to said at least one phenolic —OH group. More preferably, the hindered phenol antioxidant is an ester of 3,5-bis(1,1-dimethylethyl)-4-hydroxy-benzenepropanoic acid, and most preferably a C1-C22 linear alkyl ester of 3,5-bis(1,1-dimethylethyl)-4- hydroxy-benzenepropanoic acid. Commercially available C1-C22 linear alkyl esters of 3,5-bis(1,1-dimethylethyl)-4-hydroxy-benzenepropanoic acid include RALOX® from Raschig USA (Texas, USA), which is a methyl ester of 3,5-bis(1,1-dimethylethyl)-4-hydroxy-benzenepropanoic acid, and TINOGARD® TS from BASF (Ludwigshafen, Germany), which is an octadecyl ester of 3,5-bis(1,1-dimethylethyl)-4-hydroxy-benzenepropanoic acid.

Furthermore, the anti-oxidant used in the composition may be selected from the group consisting of α-, β-, γ-, δ-tocopherol, ethoxyquin, 2,2,4-trimethyl-1,2-dihydroquinoline, 2,6-di-tert-butyl hydroquinone, tert-butyl hydroxyanisole, lignosulphonic acid and salts thereof, and mixtures thereof. It is noted that ethoxyquin (1,2-dihydro-6-ethoxy-2,2,4-trimethylquinoline) is marketed under the name Raluquin™ by the company Raschig™.

Other types of anti-oxidants that may be used in the composition are 6-hydroxy-2,5,7,8-tetramethylchroman-2-carboxylic acid (Trolox™) and 1,2-benzisothiazoline-3-one (Proxel GXL™).

A further class of anti-oxidants which may be suitable for use in the composition is a benzofuran or benzopyran derivative having the formula:

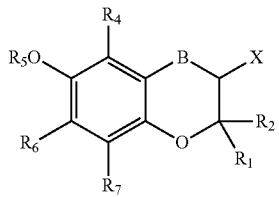

wherein $R_1$ and $R_2$ are each independently alkyl or $R_1$ and $R_2$ can be taken together to form a $C_5$-$C_6$ cyclic hydrocarbyl moiety; B is absent or $CH_2$; $R_4$ is $C_1$-$C_6$ alkyl; $R_5$ is hydrogen or $-C(O)R_3$ wherein $R_3$ is hydrogen or $C_1$-$C_{19}$ alkyl; $R_6$ is $C_1$-$C_6$ alkyl; $R_7$ is hydrogen or $C_1$-$C_6$ alkyl; X is $-CH_2OH$, or $-CH_2A$ wherein A is a nitrogen comprising unit, phenyl, or substituted phenyl. Preferred nitrogen comprising A units include amino, pyrrolidino, piperidino, morpholino, piperazino, and mixtures thereof.). The cleaning compositions of the present disclosure may comprise tannins selected from the group consisting of gallotannins, ellagitannins, complex tannins, condensed tannins, and combinations thereof.

Hygiene Agent:

The compositions of the present invention may also comprise components to deliver hygiene and/or malodor benefits such as one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag+ or nano-silver dispersions.

The cleaning compositions of the present invention may also contain antimicrobial agents. Cationic active ingredients may include but are not limited to n-alkyl dimethyl benzyl ammonium chloride, alkyl dimethyl ethyl benzyl ammonium chloride, dialkyl dimethyl quaternary ammonium compounds such as didecyl dimethyl ammonium chloride, N,N-didecyl-N-methyl-poly(oxyethyl) ammonium propionate, dioctyl didecyl ammonium chloride, also including quaternary species such as benzethonium chloride, alkyl pyridinium chlorides, and quaternary ammonium compounds with inorganic or organic counter ions such as bromine, carbonate or other moieties including dialkyl dimethyl ammonium carbonates, as well as antimicrobial amines such as Chlorhexidine Gluconate, PHMB (Polyhexamethylene biguanide), salt of a biguanide, a substituted biguanide derivative, an organic salt of a quaternary ammonium containing compound or an inorganic salt of a quaternary ammonium containing compound or mixtures thereof. More Preferably, the anti-microbial agent is selected from the group consisting of 4-4'-dichloro-2-hydroxy diphenyl ether ("Diclosan"), 2,4,4'-trichloro-2'-hydroxy diphenyl ether ("Triclosan"), and a combination thereof. Most preferably, the anti-microbial agent is 4-4'-dichloro-2-hydroxy diphenyl ether, commercially available from BASF, under the trademark name Tinosan® HP100.

Example Compositions

| Raw Material | Comp. A % wt | Comp. B % wt | Comp. C % wt | Comp. D % wt | Comp. E % wt | Comp. F % wt | Comp G % wt | Comp. H % wt |
| --- | --- | --- | --- | --- | --- | --- | --- | --- |
| Branched Alkyl Sulfate | 0 | 5.3 | 0 | 2 | 0 | 0 | 0 | 0 |
| Sodium Lauryl Sulfate | 0 | 3 | 0 | 2 | 10.4 | 2.8 | 0 | 0 |
| linear alkylbenzene sulfonate | 18 | 5 | 6 | 5 | 1.6 | 13.4 | 15 | 4 |
| AE3S Ethoxylated alkyl sulphate with an average degree of ethoxylation of 3 | 5 | 0 | 1.3 | 0 | 0 | 0 | 2 | 12 |
| C25AES Ethoxylated alkyl sulphate with an average degree of ethoxylation of 2.5[1] | 0 | 3 | 1.4 | 0 | 17 | 4 | 0 | 0 |
| amine oxide | 0.7 | 1 | 0.4 | 1 | 3.6 | 0 | 0.7 | 0 |
| Novel 1214-9 | 8.4 | 11 | 12.9 | 11 | 2.9 | 13.4 | 10 | 6 |
| citric acid | 2.9 | 2.3 | 0.7 | 2.3 | 0.8 | 4.7 | 0.9 | 1 |
| palm kernel fatty acid | 0 | 1 | 0 | 1 | 0 | 3.9 | 0 | 0 |
| topped kernel fatty acid | 2.9 | 0 | 2.3 | 0 | 0 | 0 | 3 | 5.2 |

| Raw Material | Comp. A % wt | Comp. B % wt | Comp. C % wt | Comp. D % wt | Comp. E % wt | Comp. F % wt | Comp G % wt | Comp. H % wt |
|---|---|---|---|---|---|---|---|---|
| Mannanase | 0.0017 | 0.0017 | 0.0017 | 0.0017 | 0.0015 | 0.0028 | 0 | 0 |
| Pectawash | 0.00342 | 0.00342 | 0.00342 | 0.00342 | 0.003 | 0.0034 | 0 | 0 |
| Amylase | 0.00766 | 0.00766 | 0.00766 | 0.00766 | 0.0059 | 0.0173 | 0.0059 | 0 |
| Protease | 0.07706 | 0.07706 | 0.07706 | 0.07706 | 0.0343 | 0.0916 | 0.04 | 0 |
| Nuclease[3] | 0.01 | 0.01 | 0.01 | 0.01 | 0 | 0 | 0 | 0 |
| Sodium tetraborate | 0 | 1.7 | 0 | 1.7 | 0.95 | 2.56 | 0 | 0 |
| MEA-Boric Acid Salt | 0 | 0 | 0.8 | 0 | 0 | 0 | 1 | 1.3 |
| calcium/sodium formate | 0 | 0.04 | 0.01 | 0.04 | 0.04 | 1.039 | 0 | 0 |
| Sodium/Calcium Chloride | 0.04 | 0.02 | 0.03 | 0.02 | 0.003 | 0.02 | 0.05 | 0.06 |
| Ethoxylated polyethyleneimine[2] | 0 | 2 | 1.1 | 2 | 2.8 | 0.26 | 1.6 | 0.4 |
| Amphiphilic graft copolymer | 1.5 | 0 | 0 | 0 | 0 | 0 | 0 | 0 |
| Ethoxylated-Propoxylated polyethyleneimine | 0 | 2 | 0.8 | 2 | 0.55 | 1.8 | 1.2 | 0 |
| Zwitterionic polyamine | 0.5 | 0 | 0 | 0 | 0 | 0 | 0 | 0 |
| Nonionic polyester terephthalate | 1 | 1 | 1 | 1 | 0 | 0.5 | 0 | 0 |
| DTPA | 0 | 0.1 | 0.2 | 0.1 | 0.5 | 0.7 | 0.5 | 0.25 |
| EDDS | 0.1 | 0 | 0 | 0 | 0 | 0 | 0 | 0 |
| GLDA | 0.4 | 0.3 | 0.1 | 0.3 | 0 | 0 | 0 | 0 |
| MGDA | 0.2 | 0 | 0 | 0 | 0 | 0 | 0 | 0 |
| diethylene triamine penta(methyl phosphonic) acid (DTPMP) | 1.1 | 0 | 0 | 0 | 0 | 0 | 0 | 0 |
| Fluorescent Brightener[8] | 0.06 | 0.22 | 0.03 | 0.22 | 0.04 | 0.26 | 0 | 0.039 |
| Ethanol | 0.7 | 1.9 | 0 | 1.9 | 0.42 | 2.34 | 0 | 1.5 |
| propylene glycol | 5.5 | 5.5 | 0.33 | 5.5 | 0.55 | 11.2 | 0 | 6 |
| Sorbitol | 0.01 | 0.01 | 0 | 0.01 | 0 | 0 | 0 | 0 |
| monoethanolamine | 0.2 | 0.2 | 0.6 | 0.2 | 3.77 | 0.00 | 0.8 | 0.5 |
| DETA | 0.1 | 0.08 | 0 | 0.08 | 0.05 | 0.094 | 0.1 | 0 |
| Antioxidant 1 | 0 | 0.1 | 0.1 | 0.1 | 0.04 | 0.07 | 0.07 | 0 |
| Antioxidant 2 | 0.1 | 0 | 0 | 0 | 0 | 0 | 0 | 0 |
| Hygiene Agent[6] | 0 | 0 | 0.05 | 0 | 0 | 0 | 0.04 | 0 |
| NaOH | 4.7 | 4.7 | 1.1 | 4.7 | 0.04 | 2.3 | 2.7 | 1.7 |
| NaCS | 3.2 | 1.7 | 3.2 | 1.7 | 2 | 0.0 | 6.6 | 1.4 |
| Hydrogenated Castor Oil | 0.2 | 0.1 | 0.12 | 0.1 | 0.082 | 00 | 0.8 | 0.14 |
| aesthetic dye | 0.1 | 0.01 | 0.006 | 0.01 | 0.005 | 0.017 | 0.0077 | 0.004 |
| Leuco dye | 0.05 | 0.01 | 0 | 0.01 | 0 | 0.017 | 0 | 0 |
| Perfume | 2 | 1.3 | 0.5 | 1.3 | 0.29 | 1.3 | 0.55 | 1 |
| Perfume microcapsules | 0.5 | 0.05 | 0.1 | 0.05 | 0 | 0.0 | 0 | 0.24 |
| silicone antifoam[7] | 0.02 | 0.01 | 0 | 0.01 | 0.2 | 0.0 | 0.0024 | 0.01 |
| phenyloxyethanol | 0.002 | 0.01 | 0 | 0.01 | 0 | 0.001 | 0 | 0 |
| Hueing dye | 0.01 | 0.1 | 0.05 | 0.1 | 0.026 | 0 | 0.02 | 0 |
| Sodium Bisulfite | 0 | 0 | 0 | 0 | 0 | 0.0 | 0 | 0.1 |
| water & miscellaneous | balance | balance | balance | balance | balance | balance | balance | balance |

[1] C12-15EO2.5S AlkylethoxySulfate where the alkyl portion of AES includes from about 13.9 to 14.6 carbon atoms
[2] PE-20 commercially available from BASF
[3] Nuclease enzyme is as claimed in co-pending European application 19219568.3
[4] Antioxidant 1 is 3,5-bis(1,1-dimethylethyl)-4-hydroxybenzenepropanoic acid, methyl ester [6386-38-5]
[5] Antioxidant 2 is Tinogard TS commercially available from BASF
[6] Hygiene Agent is agent is Tinosan HP 100 commercially available from BASF
[7] Dow Corning supplied antifoam blend 80-92% ethylmethyl, methyl(2-phenyl propyl)siloxane; 5-14% MQ Resin in octyl stearate a 3-7% modified silica or AF8017 supplied by Dow Corning
[8] Fluorescent Brightener is disodium 4,4'-bis{[4-anilino-6-morpholino-s-triazin-2-yl]-amino}-2,2'-stilbenedisulfonate or 2,2'-([1,1'-Biphenyl]-4,4'-diyldi-2,1-ethenediyl)bis-benzenesulfonic acid disodium salt.

Stain Removal

Technical stain swatches of CW120 cotton containing CFT ASTM Dust Sebum PCS94, CFT Discriminating Sebum PCS132 were purchased from Advanced Product Design Co., Inc (Cincinnati, Ohio). The swatches were washed in a Whirlpool® top loader washing machine (standard 64-liter wash cycle), using 7 grains per gallon water hardness and washed at 86 degrees Fahrenheit. Linear Alkyl Benzene Sulfonate and Nonionic surfactant were mixed in a 2:1 ratio. The total amount of surfactant in the wash was 200 ppm. Illustrate in the table below.

| Raw Material | Sample I: C12/C14 EO7 (Broad Range) Ethoxylation Composition Wash concentration (ppm) | Sample II: Inventive C12/C14 EO9 with Novel (Narrow Range) Ethoxylation Composition Wash concentration (ppm) | Sample III: Inventive C12/C14 EO11 with Novel (Narrow Range) Ethoxylation Composition Wash concentration (ppm) | Sample IV: Inventive C12/C14 EO13 with Novel (Narrow Range) Ethoxylation Composition Wash concentration (ppm) |
|---|---|---|---|---|
| Alfonic 1214-7 | 67 | | | |
| Novel Ziegler 1214-13 | | | | 67 |
| Novel Ziegler 1214-11 | | | 67 | |
| Novel Ziegler 1214-9 | | 67 | | |
| C11.8 HLAS | 133 | 133 | 133 | 133 |

| Raw material | Sample V: Broad Range Ethoxylation Wt % | Sample VI: Narrow Range Ethoxylation Wt % |
|---|---|---|
| Alfonic 1214-7 | 19.8 | |
| Novel Ziegler 1214-9 | | 19.8 |
| C11.8 HLAS | 20.3 | 20.3 |
| Fatty acid | 2.0 | 2.0 |
| Citric acid | 0.6 | 0.6 |
| MEA-Tetraborate | 1.0 | 1.0 |
| Magnesium Chloride | 0.02 | 0.02 |
| Sodium Chloride | 0.003 | 0.003 |
| Ethoxylated polyethyleneimine[1] | 1.7 | 1.7 |
| Ethoxylated-Propoxylated polyethyleneimine | 1.2 | 1.2 |
| Fluorescent Brightener 49 | 0.04 | 0.04 |
| Hygiene agent[2] | 0.04 | 0.04 |
| Propylene Glycol | 9.81 | 9.81 |
| Sodium Cumene Sulfonate | 2.96 | 2.96 |
| NaOH | 2.97 | 2.97 |
| MEA | 0.064 | 0.064 |
| Hydrogenated Castor Oil | 0.08 | 0.08 |
| Silicone antifoam | 0.003 | 0.003 |
| Perfume microcapsules | 0.24 | 0.24 |
| Perfume | 0.55 | 0.55 |
| aesthetic dye | 0.0077 | 0.0077 |
| water & miscellaneous | Balance | Balance |

[1] PE-20 commercially available from BASF
[2] Hygiene agent is Tinosan HP100 commercially available from BASF Image analysis was used to compare each stain to an unstained fabric control. Software converted images taken into standard colorimetric values and compared these to standards based on the commonly used Macbeth Colour Rendition Chart, assigning each stain a colorimetric value (Stain Level). Eight replicates of each were prepared.

Stain removal from the swatches was measured as follows:

Stain Removal Index (SRI) = $\Delta E_{initial} - E_{washed} \times 100$ $\Delta E_{initial}$ $\Delta E_{initial}$ = Stain level before washing $\Delta E_{washed}$ = Stain level after washing Stain removal index scores for each stain were calculated and are listed in the table below:

| | Sample I Delta SRI Vs Sample I | Sample II Delta SRI Vs Sample I | Sample III Delta SRI Vs Sample I | Sample IV Delta SRI Vs Sample I |
|---|---|---|---|---|
| PCS 132 Sebum | 0.0 | +2.1 | +1.8 | +2.3 |
| PCS94 Dust Sebum | 0.0 | +4.1 | +3.7 | +4.5 |

These results illustrate the surprising stain removal advantages on PCS132 Sebum and PCS94 Dust Sebum of the present disclosure (as used in Samples II, III, and IV) as compared to broad range peaked nonionic ethoxylates (as used in Sample I)

Technical stain swatches of CW120 cotton containing CFT ASTM Dust Sebum PCS94, CFT Discriminating Sebum PCS132 were purchased from Warwick Equest (England, United Kingdom). The swatches were washed in a Hitachi Top loading washing machine (standard 43-liter wash cycle), using 3 grains per gallon water hardness and washed at 20 degrees Celsius and two rinse cycles. Stain removal index scores for each stain were calculated and are listed in the table below.

|  | Sample V<br>Delta SRI Vs<br>Sample V | Sample VI<br>Delta SRI Vs<br>Sample V |
| --- | --- | --- |
| PCS 132 Sebum | 0.0 | +1.3 |
| PCS94 Dust Sebum | 0.0 | +6.4 |

These results illustrate the surprising stain removal advantages on PCS132 Sebum and PCS94 Dust Sebum of the present disclosure (as used in Sample VI) as compared to broad range peaked nonionic ethoxylates (as used in Sample V).

Other Examples

A. A composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 4-14, wherein less than about 20% by weight of the alcohol ethoxylate are ethoxylates having n<8.

B. The composition of paragraph A, wherein the alcohol ethoxylate of formula (I) comprises an average value of n is between 5 and 10.

C. The composition of paragraph A, wherein the alcohol ethoxylate of formula (I) comprises between 10% and about 20% by weight of the alcohol ethoxylate are ethoxylates having n=8.

D. The composition of paragraph A, wherein the alcohol ethoxylate of formula (I) wherein less than about 10% by weight of the alcohol ethoxylate are ethoxylates having n<7.

E. The composition of paragraph A, wherein the alcohol ethoxylate of formula (I) wherein the average n value is between 8 and 11.

F. The composition of paragraph A, wherein the alcohol ethoxylate of formula (I) comprises by between about 30% by weight and about 55% by weight of the alcohol ethoxylates are ethoxylates having n=9-10.

G. The composition of paragraph A, wherein the alcohol ethoxylate of formula (I) comprises greater than 80% by weight of the alcohol ethoxylate are ethoxylates having n>7.

H. The composition of paragraph A, wherein said alcohol ethoxylate is derived from a natural alcohol, a synthetic alcohol, or a mixture thereof.

I. A detergent composition comprising the composition of paragraph A, wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dishwashing detergent, a hard surface cleaner, a fabric softener composition, and mixtures thereof.

J. A composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 4-14, wherein the composition comprises between about 35% by weight and about 75% by weight of the alcohol ethoxylates are ethoxylates having n=8-11.

K. The composition of paragraph J, wherein the alcohol ethoxylate of formula (I) comprises an average value of n is between 5 and 10.

L. The composition of paragraph J, wherein the alcohol ethoxylate of formula (I) comprises between 10% and about 20% by weight of the alcohol ethoxylate are ethoxylates having n=8.

M. The composition of paragraph J, wherein the alcohol ethoxylate of formula (I) wherein less than about 10% by weight of the alcohol ethoxylate are ethoxylates having n<7.

N. The composition of paragraph J, wherein the alcohol ethoxylate of formula (I) wherein the average n value is between 6 and 9.

O. The composition of paragraph J, wherein the alcohol ethoxylate of formula (I) comprises by between about 30% by weight and about 55% by weight of the alcohol ethoxylates are ethoxylates having n=9-10.

P. The composition of paragraph J, wherein the alcohol ethoxylate of formula (I) comprises greater than 80% by weight of the alcohol ethoxylate are ethoxylates having n>7.

Q. The composition of paragraph J, wherein said alcohol ethoxylate is derived from a natural alcohol, a synthetic alcohol, or a mixture thereof.

R. A detergent composition comprising the composition of paragraph J, wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dishwashing detergent, a hard surface cleaner, a fabric softener composition, and mixtures thereof.

S. A composition comprising an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between 6-9, wherein less than about 20% by weight of the alcohol ethoxylate are ethoxylates having n<8 and wherein between about 10% by weight and about 20% by weight of the alcohol ethoxylates are ethoxylates having n=8.

T. A detergent composition comprising the composition of paragraph S, wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dishwashing detergent, a hard surface cleaner, a fabric softener composition, and mixtures thereof.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A detergent composition comprising:
    a. an alcohol ethoxylate of formula (I):

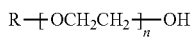

(I)

where R is selected from a saturated or unsaturated, linear or branched, $C_8$-$C_{20}$ alkyl group, where greater than 90% of n is $0 \leq n \leq 15$, and where the average value of n is between about 4 and about 14, wherein the alcohol ethoxylate of formula (I) comprises between 10% and about 20% by weight of the alcohol ethoxylate of ethoxylates having n=8; and
    b. an additional surfactant;
wherein the total amount of surfactant is from about 5% to about 60%, by weight of the detergent composition.

2. The composition of claim 1, wherein the alcohol ethoxylate of formula (I) comprises an average value of n between about 5 and about 12.

3. The composition of claim 1, wherein the alcohol ethoxylate of formula (I) comprises an average value of n between about 8 and about 11.

4. The composition of claim 1, wherein the alcohol ethoxylate of formula (I) comprises less than about 10% by weight of the alcohol ethoxylate of ethoxylates having n<7.

5. The composition of claim 1, wherein the alcohol ethoxylate of formula (I) comprises between about 30% by weight and about 55% by weight of the alcohol ethoxylates of ethoxylates having n=9-10.

6. The composition of claim 1, wherein the alcohol ethoxylate of formula (I) comprises greater than 80% by weight of the alcohol ethoxylate of ethoxylates having n>7.

7. The composition of claim 1, wherein the composition comprises between about 35% by weight and about 75% by weight of the alcohol ethoxylates of ethoxylates having n=8-11.

8. The composition of claim 1, wherein said alcohol ethoxylate is derived from a natural alcohol, a synthetic alcohol, or a mixture thereof.

9. A detergent composition comprising the composition of claim 1, wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dish-washing detergent, a hard surface cleaner, a fabric softener composition, and mixtures thereof.

10. A detergent composition comprising:
    a. an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between about 8 and about 11; wherein about 30% to about 55%, by weight of the alcohol ethoxylate have an n from about 9 to about 10 and less than 10% by weight of the alcohol ethoxylate have an n<7; and
    b. an additional surfactant;
wherein the total amount of surfactant is from about 5% to about 60%, by weight of the detergent composition.

11. The composition of claim 10, wherein the alcohol ethoxylate of formula (I) comprises about 10% to about 20% by weight of the alcohol ethoxylate where n=8.

12. A detergent composition comprising:
    a. an alcohol ethoxylate of formula (I):

(I)

where R is selected from a saturated or unsaturated, linear or branched, $C_8$-$C_{20}$ alkyl group, where greater than 90% of n is $0 \leq n \leq 15$, and where the average value of n is between about 4 and about 14, wherein less than about 20% by weight of the alcohol ethoxylate are ethoxylates having n<8 and the composition comprises between about 35% by weight and about 75% by weight of the alcohol ethoxylates of ethoxylates having n=8-11; and b. an additional surfactant;

wherein the total amount of surfactant is from about 5% to about 60%, by weight of the detergent composition.

13. The composition of claim 12, wherein the alcohol ethoxylate of formula (I) comprises between 10% and about 20% by weight of the alcohol ethoxylate of ethoxylates having n=8.

14. The composition of claim 12, wherein the alcohol ethoxylate of formula (I) comprises an average value of n between about 5 and about 12.

15. The composition of claim 12, wherein the alcohol ethoxylate of formula (I) comprises an average value of n between about 8 and about 11.

16. The composition of claim 12, wherein the alcohol ethoxylate of formula (I) comprises less than about 10% by weight of the alcohol ethoxylate of ethoxylates having n<7.

17. The composition of claim 12, wherein the alcohol ethoxylate of formula (I) comprises between about 30% by weight and about 55% by weight of the alcohol ethoxylates of ethoxylates having n=9-10.

18. The composition of claim 12, wherein the alcohol ethoxylate of formula (I) comprises greater than 80% by weight of the alcohol ethoxylate of ethoxylates having n>7.

* * * * *